(12) United States Patent
Hidaka (10) Patent No.: US 10,247,697 B2
(45) Date of Patent: Apr. 2, 2019

(54) GAS SENSOR

(71) Applicant: DENSO CORPORATION, Kariya, Aichi-pref. (JP)

(72) Inventor: Shigekazu Hidaka, Kariya (JP)

(73) Assignee: DENSO CORPORATION, Kariya (JP)

( * ) Notice: Subject to any disclaimer, the term of this patent is extended or adjusted under 35 U.S.C. 154(b) by 57 days.

(21) Appl. No.: 15/550,481

(22) PCT Filed: Feb. 9, 2016

(86) PCT No.: PCT/JP2016/053752
§ 371 (c)(1),
(2) Date: Aug. 11, 2017

(87) PCT Pub. No.: WO2016/129578
PCT Pub. Date: Aug. 18, 2016

(65) Prior Publication Data
US 2018/0031519 A1 Feb. 1, 2018

(30) Foreign Application Priority Data

Feb. 12, 2015 (JP) .................................. 2015-025776
Oct. 5, 2015 (JP) .................................. 2015-197908

(51) Int. Cl.
*G01N 27/416* (2006.01)
*G01N 27/407* (2006.01)
(Continued)

(52) U.S. Cl.
CPC ....... *G01N 27/416* (2013.01); *G01N 27/3272* (2013.01); *G01N 27/409* (2013.01);
(Continued)

(58) Field of Classification Search
CPC ............. G01N 27/416; G01N 27/4067; G01N 27/4074; G01N 27/409; G01N 27/41;
(Continued)

(56) References Cited

U.S. PATENT DOCUMENTS 4,828,671 A * 5/1989 Lin .................... G01N 27/4074
204/412
4,902,401 A * 2/1990 Lin .................... G01N 27/4074
204/412

(Continued)

FOREIGN PATENT DOCUMENTS

JP 2010-261727 11/2010

*Primary Examiner* — Susan D Leong
(74) *Attorney, Agent, or Firm* — Nixon & Vanderhye PC (57) ABSTRACT

A gas sensor includes a solid electrolyte substrate that has oxygen-ion conductivity, and a counter plate, made of ceramic, that is arranged so as to face a first surface of the solid electrolyte substrate. The gas sensor further includes a first spacer, made of ceramic, that is held between the counter plate and the solid electrolyte substrate, a heater substrate, made of ceramic, that is arranged so as to face a second surface of the solid electrolyte substrate, and a second spacer, made of ceramic, that is held between the heater substrate and the solid electrolyte substrate. Of the counter plate, the sintered density of an inside portion that comes in contact with a measurement-gas chamber is 0.8 to 5.0% lower than the sintered density of an outside portion that comes in contact with the first spacer.

4 Claims, 5 Drawing Sheets

(51) Int. Cl.
  *G01N 27/409* (2006.01)
  *G01N 27/327* (2006.01)
  *G01N 27/406* (2006.01)
  *G01N 27/41* (2006.01)
  *G01N 27/419* (2006.01)
  G01M 15/10 (2006.01)
  G01N 33/00 (2006.01)

(52) U.S. Cl.
  CPC ..... *G01N 27/4067* (2013.01); *G01N 27/4074* (2013.01); *G01N 27/41* (2013.01); *G01N 27/419* (2013.01); *G01M 15/104* (2013.01); *G01M 15/106* (2013.01); *G01N 33/0016* (2013.01)

(58) Field of Classification Search
  CPC .. G01N 27/419; G01N 27/221; G01N 27/304; G01N 27/406; G01N 27/407; G01M 15/104; G01M 15/106
  See application file for complete search history.

(56) References Cited

U.S. PATENT DOCUMENTS

| | | |
|---|---|---|
| 2005/0067283 A1 | 3/2005 | Diehl |
| 2011/0186431 A1 | 8/2011 | Horisaka et al. |
| 2012/0247957 A1 | 10/2012 | Murakami et al. |

* cited by examiner

GAS SENSOR

CROSS REFERENCE OF RELATED APPLICATIONS

This application is the U.S. national phase of International Application No. PCT/JP2016/053752 filed on Feb. 9, 2016 which designated the U.S. and claims priority to Japanese Patent Application No. 2015-25776 filed on Feb. 12, 2015, and Japanese Patent Application No. 2015-197908 filed on Oct. 5, 2015, the entire contents of each of which are hereby incorporated by reference.

TECHNICAL FIELD

The present disclosure relates to a gas sensor that is formed by layering a counter plate and a heater substrate on a solid electrolyte substrate.

BACKGROUND

Background Art

For example, a gas sensor that detects the concentration of a specific gas component such as NOx and the like is formed by layering a solid electrolyte substrate that is provided with electrodes on the surface thereof, a counter plate and first spacer that form a measurement-gas chamber, a second spacer that forms a reference-gas chamber, and a heater substrate that heats the solid electrolyte substrate. The measurement-gas chamber is formed between the solid electrolyte substrate and counter plate and is surrounded by the first spacer, and the reference-gas chamber is formed between the solid electrolyte substrate and is surrounded by the second spacer.

Moreover, when heating the solid electrolyte substrate by the heater substrate, the temperature of the measurement-gas chamber becomes a higher temperature closer toward the heater substrate. The temperature distribution inside this measurement-gas chamber has an effect on the detection precision for detecting the concentration of a specified gas. Therefore, measures have been taken to reduce the effect due to the temperature distribution.

For example, Patent Document 1 describes a gas sensor that is formed by layering a heater on a laminate of solid electrolyte layers that are provided with a measurement electrode and a reference electrode. Moreover, the reference electrode that is positioned closer to the heater than the measurement electrode is covered by a reference-gas-introducing layer that is a porous material. As a result, it becomes difficult for the heat from the heater to be transferred to the reference electrode, the temperature difference between the reference electrode and the measurement electrode is made small, and variation in the electromotive force that occurs between the reference electrode and the measurement electrode is made small.

PRIOR ART LITERATURE

Patent Literature

[Patent Document 1]
Japanese Patent Application Publication No. 2012-211863

Incidentally, when using a gas sensor, the heat from the heater substrate is transferred to the second spacer, the solid electrolyte substrate and the first spacer by heat conduction. Moreover, of the counter plate, when compared with the portion that comes in contact with the measurement-gas chamber, it is easier to heat the portion that overlaps the first spacer. The portion of the counter plate that comes in contact with the measurement-gas chamber is also easily cooled by heat dissipation to the outside. Therefore, the portion of the counter plate that comes in contact with the measurement-gas chamber is pulled by the portion of the counter plate that overlaps the first spacer, and tensile stress acts on the portion that comes in contact with the measurement-gas chamber. In some cases, there is also the possibility that cracking will occur along the boundary between the two. Even with the technology according to Patent Document 1 it is not possible to solve this problem of cracking.

In order to prevent the occurrence of cracking in the counter plate, it is possible to increase the thickness of the counter plate. However, in that case, another problem occurs in that heat from the heater is absorbed by the counter plate, and so the activation time of the gas sensor increases.

SUMMARY

Taking into consideration the background described above, it is thus desired to provide a gas sensor that together with making it difficult for cracking to occur in the counter plate, reduces the temperature distribution (temperature difference) in the measurement-gas chamber.

One form according to the present disclosure is a gas sensor that includes: a solid electrolyte substrate that has oxygen-ion conductivity; a ceramic counter plate that is arranged so as to face a first surface of the solid electrolyte substrate; a ceramic first spacer that is held between the counter plate and the solid electrolyte substrate, and forms a measurement-gas chamber between the counter plate and the solid electrolyte substrate for allowing measurement gas to flow; a ceramic heater substrate that is provided with a heat-generating layer that generates heat by electric conduction and that is arranged so as to face a second surface of the solid electrolyte substrate; and a ceramic second spacer that is held between the heat substrate and the solid electrolyte substrate, and that forms a reference-gas chamber between the heater substrate and the solid electrolyte substrate for allowing a reference gas to flow; wherein the sintered density of an inside portion of the counter plate that includes an area that comes in contact with the measurement-gas chamber is 0.8 to 5.0% lower that the sintered density of an outside portion of the counter plate that includes an area that comes in contact with the first spacer.

The inside portion may also be the entire area (portion) of the counter plate that comes in contact with the measurement-gas chamber, or may be part of the area that comes in contact with the measurement-gas chamber. Moreover, the inside portion may be the entire area of the counter plate that comes in contact with the measurement-gas chamber, and part of the area that comes in contact with the first spacer (portion that overlaps the first spacer).

BRIEF DESCRIPTION OF THE DRAWINGS

In the accompanying drawings.

DESCRIPTION OF THE EMBODIMENTS

A preferred embodiment of the gas sensor described above will be explained with reference to the drawings.

Figure 1:
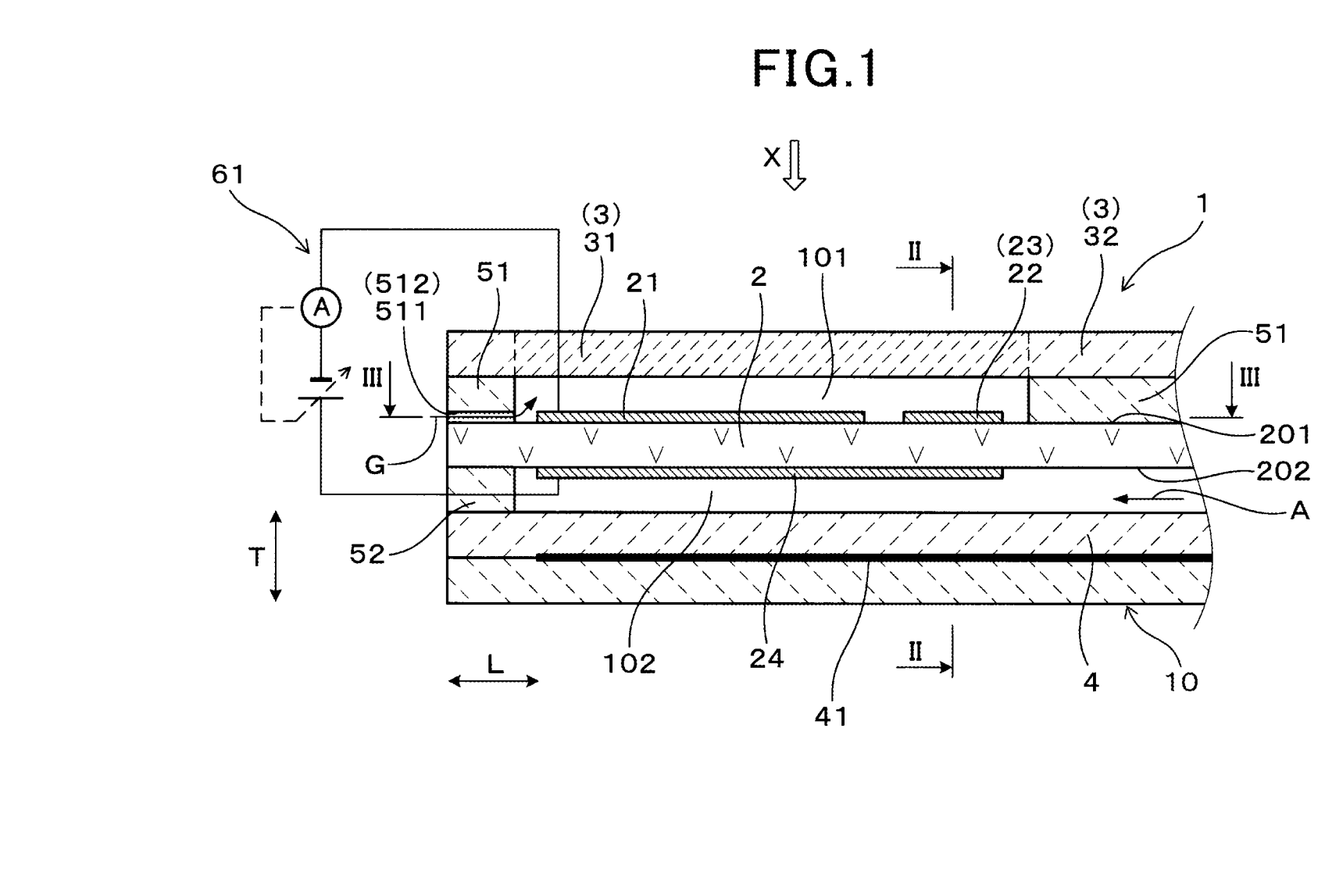
FIG. 1 is an explanatory cross-sectional view illustrating the sensor element according to an embodiment.
Figure 2:
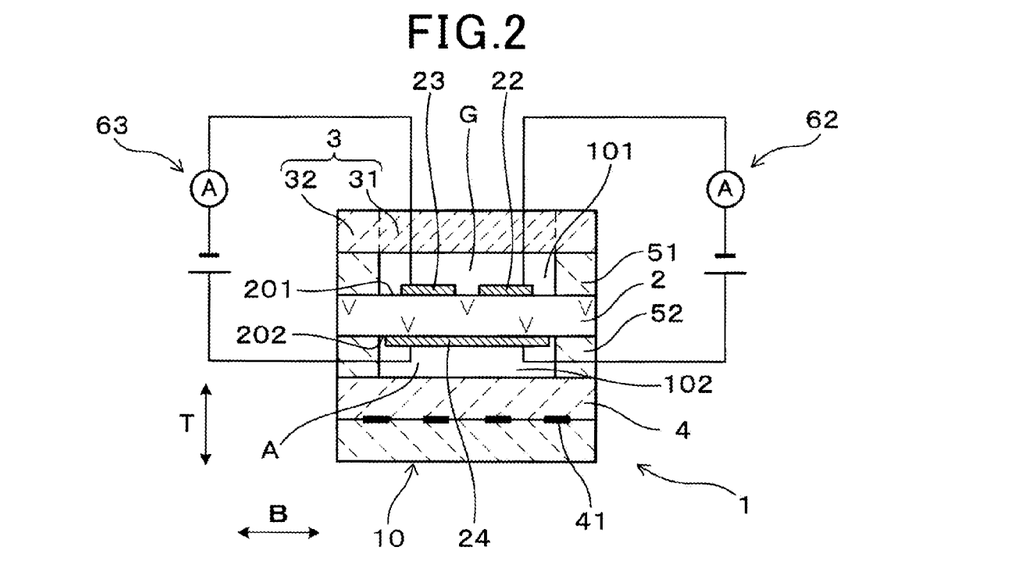
FIG. 2 is an explanatory cross-sectional view of section II-II in FIG. 1, and illustrates the sensor element according to an embodiment.
Figure 3:
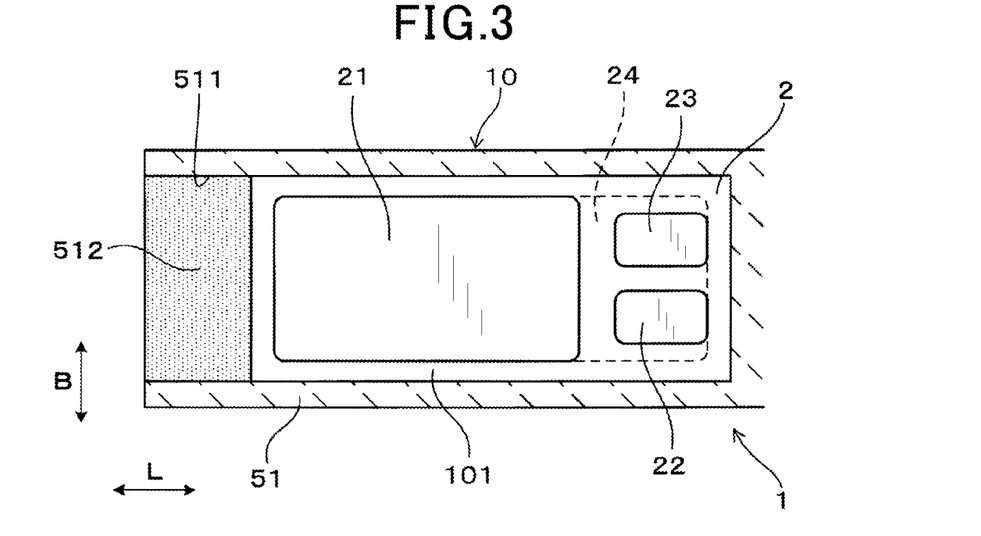
FIG. 3 is an explanatory cross-sectional view of section III-III in FIG. 1, and illustrates the sensor element according to an embodiment.

The gas sensor 1 of the embodiment, as illustrated in FIG. 1 to FIG. 3, includes a solid electrolyte substrate 2 that has oxygen-ion conductivity, a counter plate made of ceramic, a first spacer 51 made of ceramic, a heater substrate 4 made of ceramic, and a second spacer 52 made of ceramic.

Figure 4:
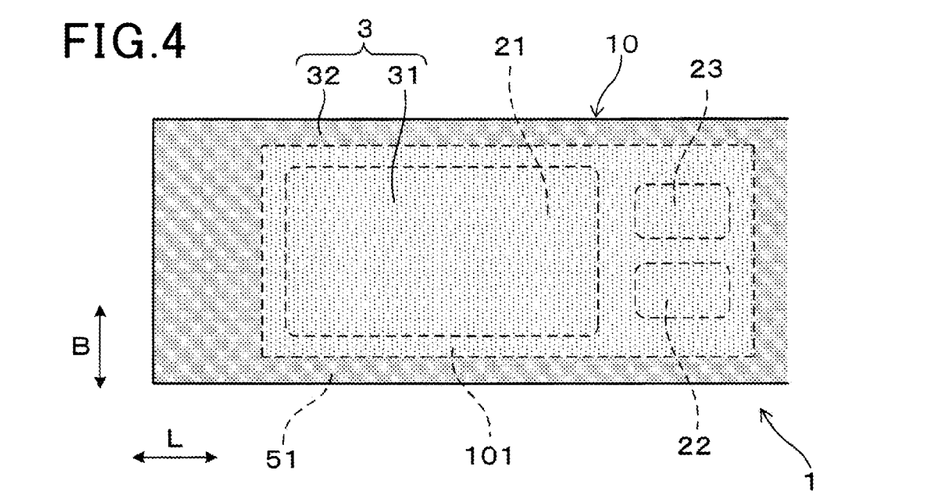
FIG. 4 is an explanatory view illustrating the sensor unit as seen from the direction of the arrow X in FIG. 1 according to an embodiment.

The counter plate 3 is arranged facing a first surface 201 of the solid electrolyte substrate 2. The first spacer 51 is held between the counter plate 3 and the solid electrolyte substrate 2, and a measurement-gas chamber 101 for allowing a measurement gas (a gas being measured) G to flow into is formed between the counter plate 3 and the solid electrolyte substrate 2. The heater substrate 4 has a heat-generating layer 41 in the inside section thereof that generates heat by electrical conduction, and is arranged facing a second surface 202 of the solid electrolyte substrate 2. The second spacer 52 is held between the heater substrate 4 and the solid electrolyte substrate 2, and a reference-gas chamber 102 for allowing a reference gas A to flow into is formed between the heater substrate 4 and the solid electrolyte substrate 2. As illustrated in FIG. 1, FIG. 2 and FIG. 4, the sintered density of the inside portion 31 that is located in the area of the counter plate 3 that comes in contact with the measurement-gas chamber 101 (in other words, the portion adjacent to the measurement-gas chamber 101) is 0.8 to 4.0% lower than the sintered density of the outside portion 32 that is located in an area that comes in contact with the first spacer 51 (in other words, the portion overlapping the first spacer 51). In the present disclosure, expressions "numerical value to numerical value" include numerical values of the boundaries.

In the following, the gas sensor 1 according to this embodiment will be explained in detail with reference to FIG. 1 to FIG. 8.

The solid electrolyte substrate 2, counter plate 3, first spacer 51, heater substrate 4 and second spacer 52 form a sensor element 10 of the gas sensor 1.

The sensor element 10 is supported by a housing via an insulator, and a cover that covers the sensor element 10 is attached to the housing. The gas sensor 1 that is formed using a sensor element 10, insulator, housing, and cover is arranged in the exhaust pipe of an internal-combustion engine. The gas sensor 1, taking the exhaust gas passing through the exhaust pipe as a measurement gas (a gas being measure) G, is used for detecting the concentration of NOx (in other words, nitrogen oxide) as a specified gas component in the exhaust gas.

As illustrated in FIG. 1 to FIG. 3, a pump electrode 21 that is used for adjusting the oxygen concentration in the measurement gas (the gas being measured) G, a monitor electrode 22 that is used for measuring the remaining oxygen concentration in the measurement gas G after adjustment of the oxygen concentration at the pump electrode 21, and a sensor electrode 23 that is used for detecting the NOx concentration in the measurement gas G after adjustment of the oxygen concentration at the pump electrode 21 are provided on the first surface of the solid electrolyte substrate 2. A reference electrode 24 that is exposed to a reference gas A that is atmospheric air is provided on the second surface 202 of the solid electrolyte substrate 2 at a position that is on the opposite side from the position where the pump electrode 21, monitor electrode 22 and sensor electrode 23 are provided. The reference electrode 24 may also be provided separately on the opposite side from where the pump electrode 21, monitor electrode 22 and sensor electrode 23 are provided.

The pump electrode 21 and the monitor electrode 22 are made using a material that displays activity with respect to oxygen, and the sensor electrode 23 is made using a material that displays activity with respect to oxygen and NOx.

As illustrated in FIG. 1 and FIG. 2, a variable voltage for keeping the oxygen concentration in the measurement gas G constant is applied between the pump electrode 21 and the reference electrode 24 by voltage application means via the solid electrolyte substrate. A specified voltage for displaying a limiting current characteristic is applied between the monitor electrode 22 and the reference electrode 24 and between the sensor electrode 23 and the reference electrode 24, via the solid electrolyte substrate 2.

A pump cell is formed by the pump electrode 21, the reference electrode 24 and the solid electrolyte substrate 2 that is held therebetween. Moreover, a monitor cell is formed by the monitor electrode 22, the reference electrode 24 and the solid electrolyte substrate that is held therebetween. Furthermore, a sensor cell is formed by the sensor electrode 23, the reference electrode 24 and the solid electrolyte substrate that is held therebetween.

In the monitor cell, by measuring the oxygen-ion current that flows between the monitor electrode 22 and reference electrode 24 via the solid electrolyte substrate 2 by electric-current-detection means 62, the remaining oxygen concentration in the measurement gas G is found. In the sensor cell, by measuring the oxygen-ion current that flows between the sensor electrode 23 and the reference electrode 24 via the solid electrolyte substrate 2 by electric-current detection means 63, the sum of the NOx concentration and remaining oxygen concentration in the measurement gas G is found. Then, by subtracting the oxygen-ion current in the monitor cell from the oxygen-ion current in the sensor cell, the NOx concentration in the measurement gas G is found.

As illustrated in FIG. 1 and FIG. 3, a gas inlet 511 for leading the measurement gas G into the measurement-gas chamber 101 is provided on the tip-end section of the sensor element 10. The gas inlet 511 is provided on the tip-end section of the first spacer 51, and a porous material 512 is arranged in the gas inlet 511 as a diffusion resistor when the measurement gas G is led into the measurement-gas chamber 101.

The measurement gas G flows inside the measurement-gas chamber 101 from the tip-end side where the gas inlet 511 is provided toward the base-end side. The pump electrode 21 is arranged at a position that is near the gas inlet 511, and the monitor electrode 22 and sensor electrode 23 are arranged side by side in the horizontal direction B further on the downstream side of the flow of the measurement gas G than the pump electrode 21 in the measurement-gas chamber 101.

The reference gas A is led into the reference-gas chamber 102 from the base-end side of the second spacer 52. The heater substrate 4 omnidirectionally encloses a heat-generating layer 41 that generates Joule heat by electric conduction.

The solid electrolyte substrate 2 is composed of materials including yttria-stabilized zirconia, and the counter plate 2, first spacer 51, second spacer 52 and heater substrate 4 are composed of materials including alumina that displays an insulating characteristic (in other words, aluminum oxide). The insulating material of the counter plate 3 and the like, besides alumina, may be aluminum nitride, silicon nitride, cordierite, mullite, steatite, forsterite and the like.

The counter plate 2, heater substrate 4, first spacer 51 and second spacer 52 are sintered bodies that are obtained by sintering (firing) a material having ceramic particles, a solvent and a binder at a specified temperature. In the sintered bodies the ceramic particles are bonded together by removing the solvent and binder and reducing the volume. The respective sintered densities of the outside portion 32 of the counter plate 3, the heater substrate 4, the first spacer 51 and the second spacer 52 are within the range 95 to 100%. As a result, it is possible to sufficiently maintain the strength of the outside portion 32, the heater substrate 4, the first spacer 51 and the second spacer 52.

Here, when the sintered density is 100%, the entire amount of solvent and binder is removed, and only ceramic particles that are bonded together remain, and the whole of the ceramic particles is called the completely reduced state. Moreover, when the sintered density is 95% for example, it is said that in this case the bulk density is 5% less than the bulk density (kg/m3) for the case in which the sintered density is 100%.

Figure 5:
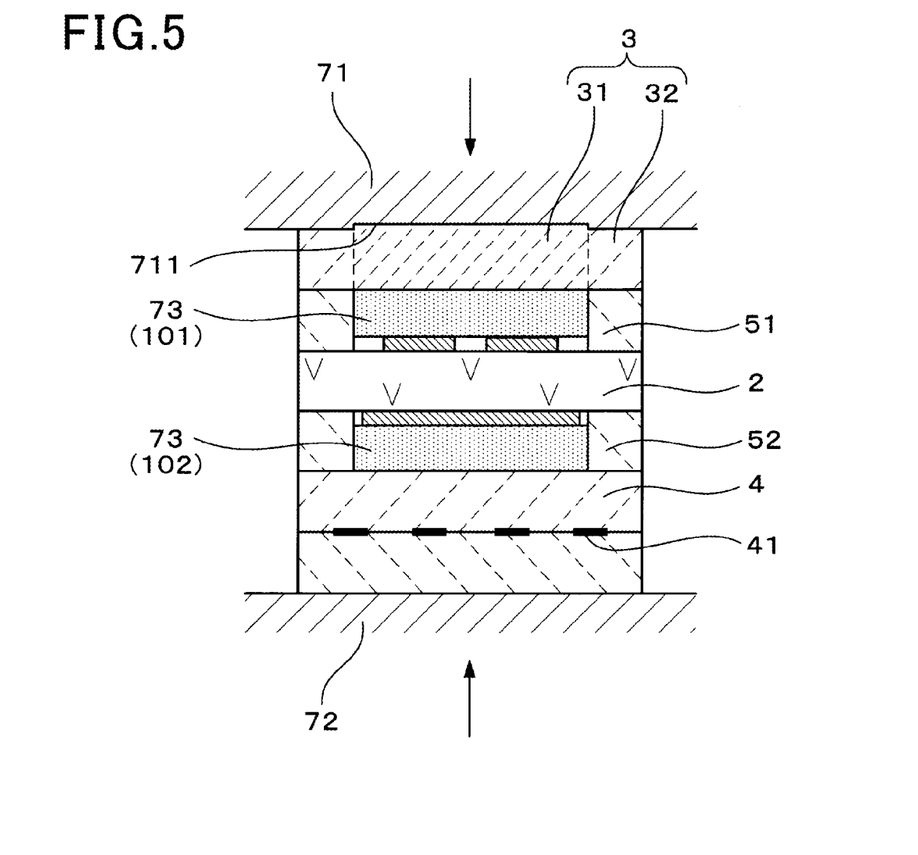
FIG. 5 is an explanatory cross-sectional view illustrating a state in which a sensor element laminate is placed between a first mold and a second mold and sintering is performed.

When manufacturing the sensor element 10, as illustrated in FIG. 5, a laminate (in other words sensor element 10) is formed by layering respective ceramic sheets of a solid electrolyte sheet that includes the solid electrolyte substrate 2, the counter plate 3, the heater substrate 4, the first spacer 51 and the second spacer 52. Moreover, in order to apply pressure to the laminate, a first mold 71 and a second mold 72 are used. A concave section 711 for reducing pressure is formed in the first mold 71 at a site that faces the inside portion 31 of the counter plate 3.

Then, the laminate is placed between the first mold 71 and the second mold 72, pressure is applied to the laminate, the laminate is heated in a state with pressure applied, and the laminate is sintered. At this time, the pressure that acts on the inside portion 31 of the counter plate 3 that faces the concave section 711 of the first mold 71 is less than the pressure that acts on the outside portion of the counter plate 3. As a result, the distance between particles of the ceramic particles of the inside portion 31 becomes larger than the distance between particles of the ceramic particles of the outside portion 32. In other words, during sintering, by the making the pressure that is applied to the inside portion less than the pressure that is applied to the outside portion, it is possible to reduce the degree of close contact between ceramic particles, and make the sintered density of the inside portion less than the sintered density of the outside portion.

Sheets 73 that are completely removed by evaporation during sintering of the laminate are placed in the space that forms the measurement-gas chamber 101, and the space that forms the reference-gas chamber 102.

Next, when the laminate is heated and the solvent and binder evaporate, the distance between particles of the ceramic particles of the inside portion 31 is maintained in a larger state than the distance between particles of the ceramic particles of the outside portion 32. As a result, when the laminate is sintered, the sintered density of the inside portion 31 of the counter plate 3 is formed so as to be 0.8 to 5.0% less than the sintered density of the outside portion 32 of the counter plate 3. In this way, the shrinkage rate during sintering of the inside portion 31 is less than that of the outside portion 32, thereby forming a portion having coarse sintered density.

As illustrated in FIG. 4, the inside portion 31 of the counter plate of this embodiment is a portion that comes in contact with the measurement-gas chamber 101. Moreover, the inside portion 31 of the counter plate 3 is the entire portion of the counter plate 3 that forms the measurement-gas chamber 101, or in other words, is the entire portion that does not overlap the first spacer 51. On the other hand, the outside portion 32 of the counter plate 3 of this embodiment is the portion that comes in contact with the first spacer 51. Moreover, the outside portion 32 of the counter plate is the entire portion of the counter plate 3 that overlaps the first spacer 51, or in other words is the entire portion that does not form the measurement-gas chamber 101. The outside portion 32 is formed in a state so as to completely surround the circumference of the inside portion.

In the counter plate of this embodiment, the width in the horizontal direction B of the measurement-gas chamber 101 is the same as the width in the horizontal direction B of the inside portion 31.

Here, in the sensor element 10, the direction in which the tip-end side and base-end side are positioned is taken to be the length direction, the direction in which the solid electrolyte substrate 2, counter plate 3, first spacer 51, heater substrate 4 and second spacer 52 are layered is taken to be the layered direction T, and the horizontal direction B is taken to be the direction that is orthogonal to the length direction L and layered direction T.

The inside portion of the counter plate 3 can also have the following configuration.

Figure 6:
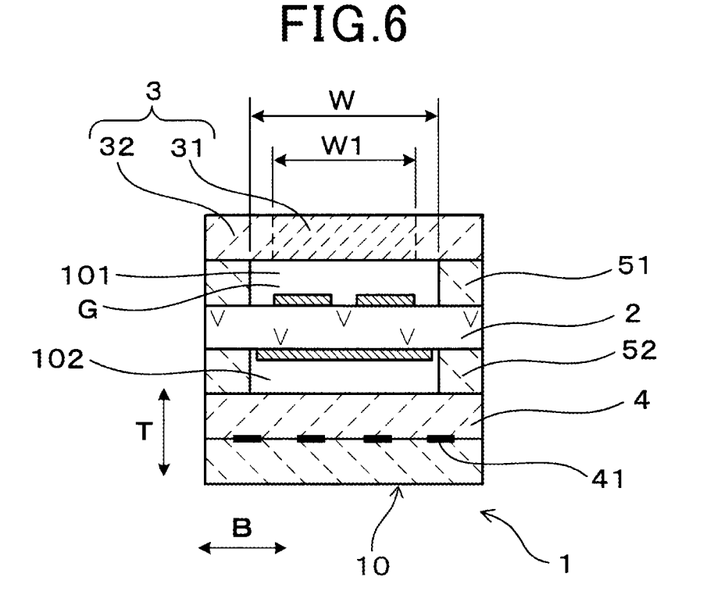
FIG. 6 is an explanatory cross-sectional view that corresponds to section II-II in FIG. 1, and illustrates another sensor element according to an embodiment.

As illustrated in FIG. 6, the inside portion 31 can be taken to be the part of the area of the counter plate 3 that comes in contact with the measurement-gas chamber 101, and the outside portion 32 can be taken to be the remaining part of the counter plate 3 that comes in contact with the measurement-gas chamber 101 and the part of the counter plate that comes in contact with the first spacer 51. In this case, when the width in the horizontal direction B of the measurement-gas chamber 101 is taken to be W, the width W1 in the horizontal direction B of the inside portion 31 is within the range of no less than 0.8 W but less than 1.0 W.

Figure 7:
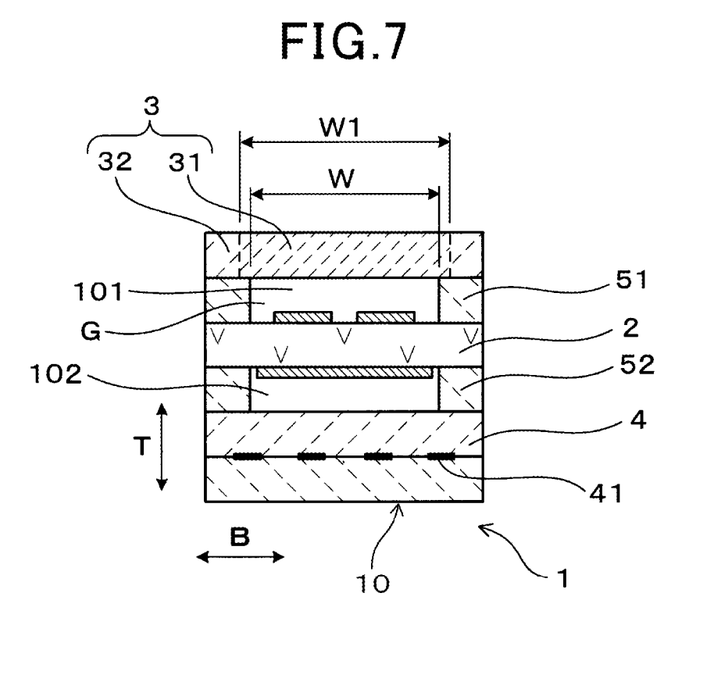
FIG. 7 is an explanatory cross-sectional view that corresponds to section II-II in FIG. 1, and illustrates another sensor element according to an embodiment.

Furthermore, as illustrated in FIG. 7, the inside portion 31 can be taken to be the entire area that comes in contact with the measurement-gas chamber 101, and part of the area of the counter plate 3 that comes in contact with the first spacer 51, and the outside portion 32 can be taken to be the remaining area of the counter plate 3 that comes in contact with the first spacer 51. In this case, when the width in the horizontal direction B of the measurement-gas chamber 101 is taken to be W, the width W1 in the horizontal direction B of the inside portion 31 is within the range greater than 1.0 W but no greater than 1.5 W.

Figure 8:
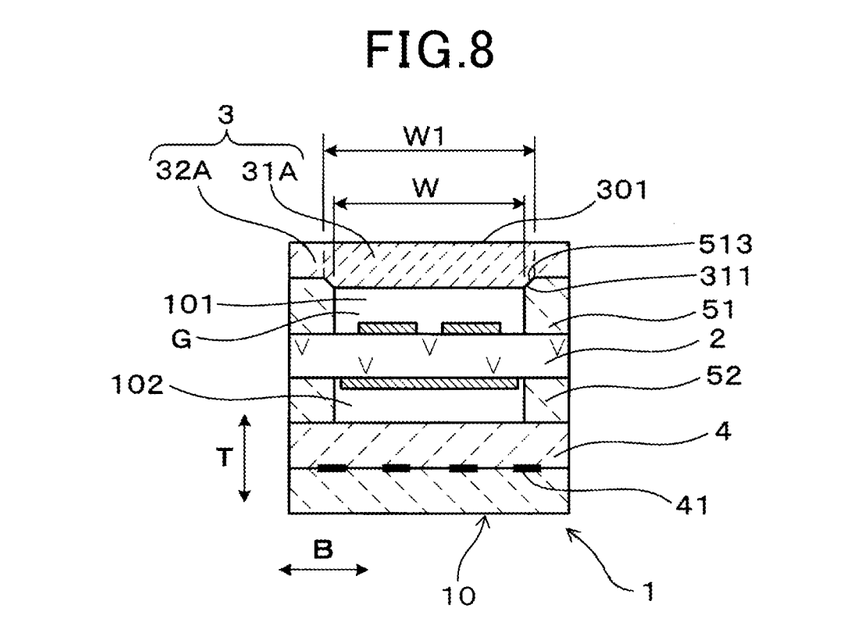
FIG. 8 is an explanatory cross-sectional view that corresponds to section II-II in FIG. 1, and illustrates another sensor element according to an embodiment.

In the case of FIG. 7, as illustrated in FIG. 8, the counter plate 3 can be formed by an inside portion 31A that is positioned on the inside, and an outside portion 32A that is positioned on the outside of the inside portion 31A and that has a thickness that is less than the inside portion 32A. The outside portion 32A is such that the thickness is reduced so that the surface that faces the first spacer 51 approaches the outside surface 301 of the counter plate 3. Moreover, the corner of the inside portion 31A on the side that faces the first spacer 51 can be formed to be a tapered surface 311, and the corner section of the first spacer 51 on the side that faces the inside portion 31 can be formed to be a tapered surface 513 that faces the tapered surface 311. In this case, it is possible to increase the boundary surface area between the counter plate 3 and the first spacer 51, and increase the percentage of the inside portion 31A having a coarse sintered density.

The gas sensor 1 of this embodiment is such that stress is intentionally generated in the counter plate 3 by partially changing the sintered density (firing density) of the counter plate.

More specifically, an inside portion 31 and an outside portion 32 are provided in the counter plate 3, and the sintered density of the inside portion 31 is 0.8 to 5.0% lower than the sintered density of the outside portion 32. By making the sintered density of the inside portion 31 less than the sintered density of the outside portion 32, it is possible to make a sensor element 10 in a state in which compressive stress is applied to the inside portion 31 from the outside portion 32.

As a result, even when thermal stress is generated when performing sintering of the sensor element 10, it is possible to constantly maintain a state in which compressive stress is generated in the end section (in other words, the boundary position of the inside portion 31 and the outside portions 32) of the area of the counter plate 3 that comes in contact with the measurement-gas chamber 10. The strength of the ceramic material against compressive stress is markedly higher than the strength of the ceramic material against tensile stress. Therefore, it is possible to make it difficult for cracking to occur in the end section of the area of the counter plate 3 that comes in contact with the measurement-gas chamber 101.

Moreover, by the sintered density of the inside portion 31 being low, the heat retention by the inside portion 31 is improved. As a result, it becomes difficult for the heat of the measurement gas G that is heated by the heating layer 41 of the heater substrate 4 to dissipate to the outside of the sensor element 10 from the inside portion 31. Moreover, the temperature distribution in the measurement-gas chamber decreases, and it is possible to improve the precision for detecting gas concentration by the gas sensor 1.

Therefore, with the gas sensor 1 of this embodiment, together with it becoming difficult for cracking to occur in the counter plate 3, it is possible to reduce the temperature distribution (or in other words, the temperature difference) in the measurement-gas chamber 101.

(Confirmation Test)

In this confirmation test, testing was performed to check the strength of the counter plate and the NOx sensitivity of the of the gas sensor 1 when the difference between the sintered density of the inside portion 31 of the counter plate 3 and the sintered density of the outside portion 32 of the counter plate 3 (called the sintered density difference) (%), and the width W1 in the horizontal direction B of the inside portion 31 with respect to the width W in the horizontal direction of the measurement-gas chamber 101 are changed.

In this confirmation test, testing is performed on test specimens 1 to 9 of which the sintered density difference is within the range 0.8% to 5.0%, and the width W1 in the horizontal direction B of the inside portion 31 is within the range 0.8 W to 1.5 W. Moreover, for comparison, testing was also performed on comparative samples 1 to 5 of which the sintered density difference and the width W1 in the horizontal direction B of the inside portion 31 are outside of the ranges above.

The strength was checked by performing a destruction test by thermal shock (in other words, a cracking occurrence confirmation test) and checking whether or not cracking occurred in the end portion of the area of the counter plate that comes in contact with the gas-measurement chamber 101. This destruction test was performed based on the Charpy impact test, and the Charpy impact value that is the required amount of energy when the end portion of the area that comes in contact with the measurement-gas chamber 101 of the sensor element 10 breaks was found. Then, with this Charpy impact value as an index, evaluation of the strength of the sensor element 10 was performed. In the strength evaluation, specimens for which cracking did not occur in the destruction test, and in an overloaded state when the Charpy value was large when cracking was intentionally made to occur were evaluated to be "Excellent"; and specimens for which cracking did not occur in the destruction test, and in an overloaded state when the Charpy value was small when cracking was intentionally made to occur were evaluated to be "Good", and specimens for which cracking occurred in the destruction test were evaluated to be "poor".

The NOx sensitivity is checked by whether or not measurement precision for measuring the NOx concentration has dropped due to temperature distribution that occurs inside the measurement-gas chamber 101. In the evaluation of the NOx sensitivity, specimens for which there is no decrease in NOx sensitivity in testing, and in an overloaded state the required energy was large when the NOx sensitivity was intentionally made to decrease were evaluated to be "Excellent"; specimens for which there is no decrease in NOx sensitivity in testing, and in an overloaded state the required energy was small when the NOx sensitivity was intentionally made to decrease were evaluated to be "Good"; and specimens for which the NOx sensitivity decreased in testing were evaluated to be "poor".

The sintered density difference and the width W1 in the horizontal direction B of the inside portion 31 of the test specimens 1 to 9 and the comparative specimens 1 to 5, and the results of performing the confirmation tests are presented in Table 1.

TABLE 1

| | Structure | | Evaluation | |
|---|---|---|---|---|
| | Sintered density difference (%) | Width W1 of inside portion | Strength test | NOx sensitivity test |
| Test specimen 1 | 0.8 | 0.8 W | Good | Good |
| Test specimen 2 | 1.0 | 0.8 W | Excellent | Excellent |
| Test specimen 3 | 3.0 | 0.8 W | Excellent | Excellent |
| Test specimen 4 | 4.0 | 0.8 W | Good | Excellent |
| Test specimen 5 | 5.0 | 0.8 W | Good | Excellent |
| Test specimen 6 | 0.8 | 1.0 W | Good | Excellent |

TABLE 1-continued

| | Structure | | Evaluation | |
|---|---|---|---|---|
| | Sintered density difference (%) | Width W1 of inside portion | Strength test | NOx sensitivity test |
| Test specimen 7 | 0.8 | 1.4 W | Good | Excellent |
| Test specimen 8 | 0.8 | 1.5 W | Good | Excellent |
| Test specimen 9 | 5.0 | 1.5 W | Good | Excellent |
| Comparative specimen 1 | non | non | Poor | Poor |
| Comparative specimen 2 | 0.7 | 0.8 W | Poor | Poor |
| Comparative specimen 3 | 6.0 | 0.8 W | Poor | Excellent |
| Comparative specimen 4 | 0.8 | 0.7 W | Poor | Poor |
| Comparative specimen 5 | 0.8 | 1.6 W | Poor | Excellent |

For the test specimens 2 and 3 having a sintered density difference of 1.0% or 3.0% and width W1 in the horizontal direction B of the inside portion 31 of 0.8 W, the strength and NOx sensitivity were both "Excellent". From this result it can be seen that from the aspect of strength and NOx sensitivity, a sintered density difference of 1.0 to 3.0% is most preferred.

Moreover, for the test specimens 1 and 4 to 9 having a sintered density difference of 0.8%, 4.0% or 5.0%, and a width W1 in the horizontal direction B of the inside portion 31 of 0.8 W, 1.0 W, 1.4 W and 1.5 W, the strength was "Good" and the NOx sensitivity was "Excellent". From this result it can be seen that by the sintered density difference being within the range 0.8% to 5.0%, and the width W1 in the horizontal direction B of the inside portion 31 being 0.8 W to 1.5 W, both the strength and the NOx sensitivity are excellent.

On the other hand, for comparative specimen 1 having no sintered density difference (in other words, 0%), and no inside portion 31 (the width W1 in the horizontal direction B of the inside portion is 0), and for comparative specimens 2 to 5 having a sintered density difference of less than 0.8% or greater than 5.0%, or a width W1 in the horizontal direction B of the inside portion that is less than 0.8 W or greater than 1.5 W, at least one of the strength and NOx sensitivity becomes "poor". From this result it can be seen that when the sintered density difference is less than 0.8% or greater than 5.0%, or when the width W1 in the horizontal direction B of the inside portion 31 is less than 0.8 W or greater than 1.5 W, there is a possibility that cracking will occur in the end portion of the area of the counter plate 3 that comes in contact with the measurement-gas chamber 101, or there is a possibility that the detection precision for detecting the NOx concentration will decrease.

DESCRIPTION OF THE REFERENCE NUMBERS

1 Gas sensor
10 Sensor element
101 Measurement-gas chamber
102 Reference-gas chamber
2 Solid electrolyte substrate
201 First surface
202 Second surface
3 Counter plate
31 Inside portion
32 Outside portion
4 Heater substrate
41 Heat-generating layer
51 First spacer
52 Second spacer
G Gas being measured (measurement gas)
A Reference gas

What is claimed is:

1. A gas sensor, comprising:
a solid electrolyte substrate that has oxygen-ion conductivity;
a counter plate, made of ceramic, that is arranged so as to face a first surface of the solid electrolyte substrate;
a first spacer, made of ceramic, that is held between the counter plate and the solid electrolyte substrate, and forms a measurement-gas chamber between the counter plate and the solid electrolyte substrate for allowing a measurement gas to flow;
a heater substrate, made of ceramic, that is provided with a heat-generating layer that generates heat by electrical conduction and that is arranged so as to face a second surface of the solid electrolyte substrate; and
a second spacer, made of ceramic, that is held between the heat substrate and the solid electrolyte substrate, and that forms a reference-gas chamber between the heater substrate and the solid electrolyte substrate for allowing a reference gas to flow; wherein
the sintered density of an inside portion of the counter plate that includes an area that comes in contact with the measurement-gas chamber is 0.8 to 5.0% lower that the sintered density of an outside portion of the counter plate that includes an area that comes in contact with the first spacer.

2. The gas sensor according to claim 1, wherein the sintered density of the outside portion is 95 to 100%.

3. The gas sensor according to claim 1, wherein when the width of the measurement-gas chamber is taken to be W, the width (W1) of the inside portion is within a range of 0.8 to 1.5 W.

4. The gas sensor according to claim 2, wherein when the width of the measurement-gas chamber is taken to be W, the width (W1) of the inside portion is within a range of 0.8 to 1.5 W.

* * * * *